United States Patent
Baxi et al.

(10) Patent No.: US 9,885,677 B2
(45) Date of Patent: Feb. 6, 2018

(54) LIQUID QUALITY METER APPARATUS

(71) Applicant: Intel Corporation, Santa Clara, CA (US)

(72) Inventors: Amit S. Baxi, Thane (IN); Vincent S. Mageshkumar, Navi Mumbai (IN)

(73) Assignee: Intel Corporation, Santa Clara, CA (US)

( * ) Notice: Subject to any disclaimer, the term of this patent is extended or adjusted under 35 U.S.C. 154(b) by 791 days.

(21) Appl. No.: 14/286,774

(22) Filed: May 23, 2014

(65) Prior Publication Data

US 2015/0338359 A1 Nov. 26, 2015

(51) Int. Cl.
| | | |
|---|---|---|
| G01K 7/00 | (2006.01) | |
| G01N 25/00 | (2006.01) | |
| G01N 25/72 | (2006.01) | |
| G01N 27/02 | (2006.01) | |
| G01N 27/07 | (2006.01) | |
| G01N 27/04 | (2006.01) | |
| G01N 33/18 | (2006.01) | |
| G01N 27/06 | (2006.01) | |

(52) U.S. Cl.
CPC .......... *G01N 25/72* (2013.01); *G01N 27/028* (2013.01); *G01N 27/045* (2013.01); *G01N 27/07* (2013.01); *G01N 33/1886* (2013.01); *G01N 27/06* (2013.01)

(58) Field of Classification Search
USPC .................................. 374/170, 43–45, 142
See application file for complete search history.

(56) References Cited

U.S. PATENT DOCUMENTS

| | | | | |
|---|---|---|---|---|
| 4,686,857 A | * | 8/1987 | Kato | G01N 27/06 324/698 |
| 4,853,638 A | * | 8/1989 | Endou | G01N 27/06 204/408 |
| 6,664,793 B1 | * | 12/2003 | Sampson | G01N 27/221 324/439 |

(Continued)

FOREIGN PATENT DOCUMENTS

| | | |
|---|---|---|
| JP | 2003194768 A | 7/2003 |
| JP | 2005351688 A * | 12/2005 |

(Continued)

OTHER PUBLICATIONS

Translation of JP 2005-351688 A, Dec. 22, 2005.*

(Continued)

*Primary Examiner* — Mirellys Jagan
(74) *Attorney, Agent, or Firm* — Schwabe, Williamson & Wyatt, P.C.

(57) ABSTRACT

Embodiments of the present disclosure provide techniques and configurations for an apparatus for providing liquid quality measurements. In one instance, the apparatus may comprise a printed circuit board (PCB) having first and second electrodes associated with the PCB, to directly contact with a liquid to obtain a plurality of electrical parameters of the liquid when electrical current passes between the first and second electrodes while in contact with the liquid, wherein the electrical parameters are associated with quality of the liquid. The PCB may further comprise circuitry disposed thereon and coupled to the first and second electrodes to collect the electric parameters of the liquid. Other embodiments may be described and/or claimed.

12 Claims, 10 Drawing Sheets

(56) References Cited

U.S. PATENT DOCUMENTS

| | | | | |
|---|---|---|---|---|
| 8,179,141 | B2* | 5/2012 | Rajagopalan | G01N 27/06 324/439 |
| 2002/0167322 | A1 | 11/2002 | He et al. | |
| 2003/0098690 | A1* | 5/2003 | Higo | G01N 27/06 324/439 |
| 2014/0070826 | A1* | 3/2014 | Grass | F01N 3/2066 324/693 |
| 2014/0132288 | A1* | 5/2014 | Kim | G01N 27/06 324/693 |

FOREIGN PATENT DOCUMENTS

| | | | |
|---|---|---|---|
| JP | 2006349551 | A | 12/2006 |
| JP | 2007155226 | A | 6/2007 |
| JP | 4866304 | B2 | 2/2012 |

OTHER PUBLICATIONS

International Preliminary Report on Patentability dated Dec. 8, 2016, issued in corresponding International Application No. PCT/US2015/027467, 10 pages.

International Search Report and Written Opinion dated Jul. 29, 2015, issued in corresponding Application International No. PCT/US2015/027467, 13 pages.

Notice of Preliminary Rejection received Jun. 29, 2017, and dated Jun. 9, 2017, issued in Korean Patent Appln. No. 2016-7029229, 13 pages.

* cited by examiner

LIQUID QUALITY METER APPARATUS

FIELD

Embodiments of the present disclosure generally relate to the field of sensor devices, and more particularly, to liquid quality sensor devices that may integrate with portable special purpose or computing devices.

BACKGROUND

Pollution of drinking water is an important cause of health problems worldwide. Excessive use of fertilizers, pesticides, and industrial waste has caused biochemical contamination of surface water as well as ground water or other viably important liquids. Presence of these chemicals and salts in excessive amounts in water may cause undesired health effects in humans and animals. Accordingly, liquid (e.g., water) quality control may be critical at least in some areas of the world.

The amount of total dissolved salts (TDS) in water is a gross indicator of water quality and may indicate aggregate contamination. Today, devices such as water quality meters are used to measure TDS or other quality indicators of water or other liquids. The conventional liquid (e.g., water) quality meter devices may include metal graphite-based electrodes and metal-rod encapsulated water temperature sensors. Existing liquid quality meter devices may be expensive, bulky, and difficult to use.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

DETAILED DESCRIPTION

Figure 1:
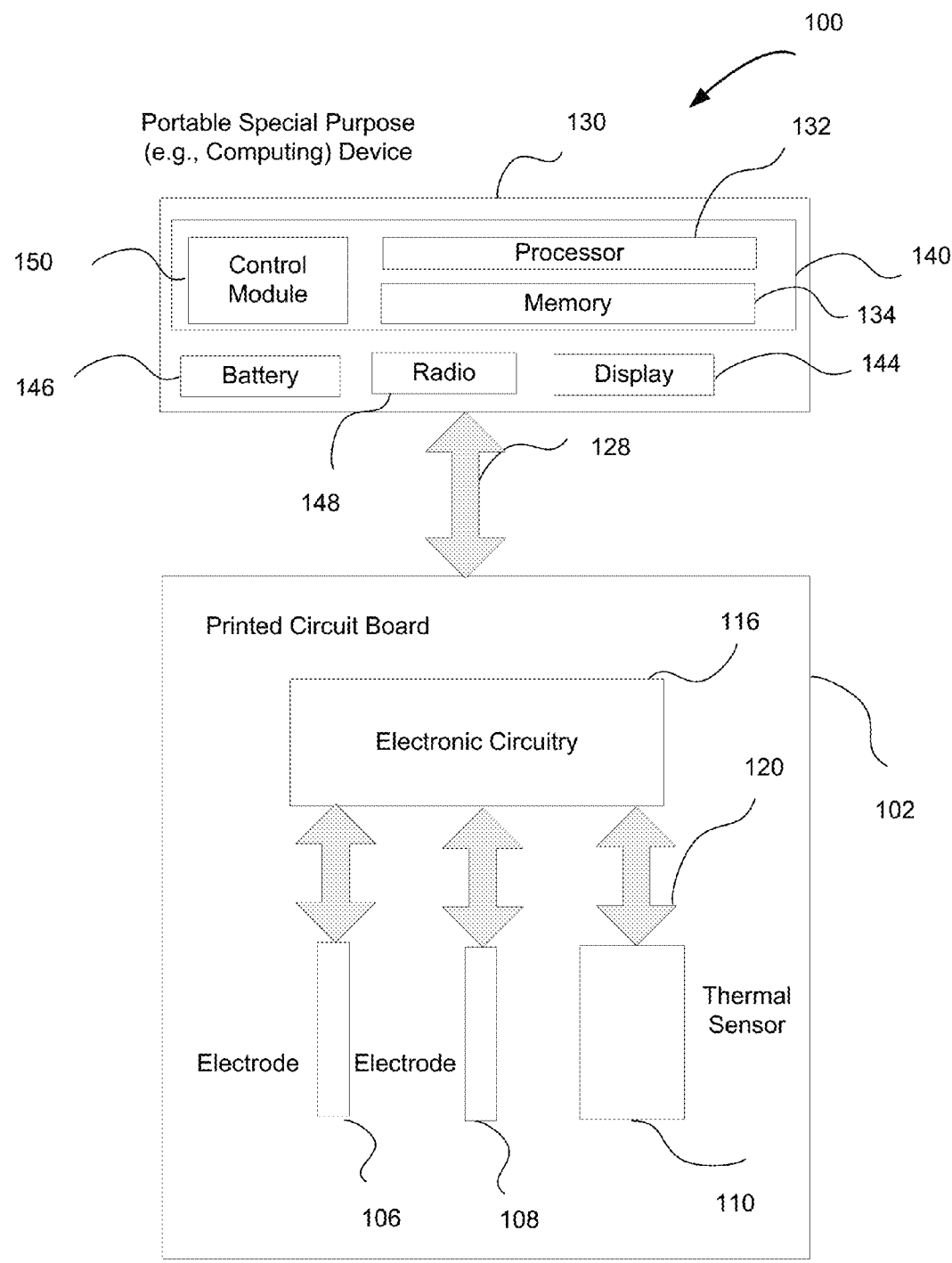
FIG. 1 schematically illustrates an example liquid quality meter device for measuring liquid quality in accordance with some embodiments.

Embodiments of the present disclosure include techniques and configurations for liquid quality meter devices. In accordance with embodiments, an apparatus for liquid quality measurements may be associated with a printed circuit board (PCB) and may be suitable for integrating with a computing device, such as a smartphone. The apparatus's electrodes for measuring liquid's electrical parameters may be patterned on a PCB (e.g., a PCB substrate). The PCB may be covered to prevent direct contact with the liquid, with the electrodes exposable to directly contact the liquid. A thermal sensor for measuring thermal parameters of the liquid may be also mounted on the PCB and covered (e.g., encapsulated), to prevent direct contact with the liquid and at the same time thermally expose the sensor for thermal measurements of the liquid. In some instances, the apparatus for liquid quality measurements may be patterned on the same PCB that includes the computing device's electronic components, or on a separate PCB integrated (e.g., communicatively coupled) with the computing device.

In the following detailed description, reference is made to the accompanying drawings that form a part hereof, wherein like numerals designate like parts throughout, and in which are shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical, electrical, or optical contact. However, "coupled" may also mean that two or more elements indirectly contact each other, but yet still cooperate or interact with each other, and may mean that one or more other elements are coupled or connected between the elements that are said to be coupled with each other. The term "directly coupled" may mean that two or more elements are in direct contact.

FIG. 1 schematically illustrates an example liquid quality meter apparatus 100 for measuring liquid quality in accordance with some embodiments of the present disclosure. In some embodiments, the apparatus 100 may comprise a special purpose device configured to provide liquid quality measurements. In some embodiments, the apparatus 100 may comprise a multi-purpose device, such as a computing device, having the functionalities providing liquid quality measurements integrated with the computing device. The computing device may include a portable or mobile computing device, such as a smartphone, a laptop, a tablet, a netbook, an ultrabook, etc.

Accordingly, the apparatus 100 may comprise a computing device 130 with integrated liquid quality measurement functionalities implemented on a PCB 102. The PCB 102 may be integrated (e.g., communicatively coupled 128) with the computing device 130. The PCB 102 may include first and second electrodes 106, 108 associated with (e.g., disposed on) the PCB 102 to enable direct contact of the electrodes 106, 108 with a liquid (e.g., water), to obtain (e.g., measure) one or more electrical parameters of the liquid when electrical current passes between the electrodes 106, 108 while in contact with the liquid.

For example, the electrodes 106, 108 may be patterned or embedded in the PCB 102, such as disposed on a substrate of the PCB 102 (e.g., a glass-epoxy substrate or other suitable substrate). The first and second electrodes 106, 108 may comprise traces or tracks that may be chemical or electrochemical plated, such as gold plated, for example. Chemical or electrochemical plating may reduce the polarization and corrosion of electrodes 106, 108.

The PCB 102 may further comprise a thermal sensor 110 disposed on the PCB 102 to thermally contact the liquid to obtain (e.g., measure) thermal parameters of the liquid. The PCB 102 may further comprise circuitry 116 disposed on the PCB and communicatively coupled 120 to the first and second electrodes 106, 108 and thermal sensor 110 to collect the electrical and thermal parameters of the liquid. An example implementation of the circuitry 116 will be described in reference to FIG. 2 in greater detail.

The electrical parameters and thermal parameters of the liquid may be associated with quality of the liquid, such that quality of the liquid may be determined based on these parameters. For example, electrical parameters may comprise electrical conductivity (or resistance) of the liquid, and thermal parameters may comprise temperature of the liquid. In some embodiments, the quality of the liquid may comprise a value indicating certain characteristics of the liquid content, for example, presence and/or proportion of mineral additives in the liquid or other characteristics of interest pertaining to the liquid or, more generally, liquid substances that may be of consumable or industrial nature, such as drinks, industrial and home use products (e.g., cleaning products), and the like.

In some embodiments, the liquid may include water, such as surface water of lakes, rivers or watersheds, ground water, such as water from wells or the like, or potable water from canisters, cisterns, or the like. The quality of the liquid (e.g., water) may comprise a value indicating total dissolved salts (TDS) in the liquid. TDS in the liquid (e.g., water) may be directly proportional to the electrical conductivity of the liquid, which may be measured by passing current through the liquid between the electrodes 106, 108. TDS may be mathematically derived from liquid's electrical conductivity. Electrical conductivity of the liquid may be influenced by the temperature of the liquid. Accordingly, liquid temperature may be also measured using a separate thermal sensor (e.g., 110) for temperature compensation. Thus, the value indicating liquid quality may be determined based on (e.g., mathematically derived from) electrical conductivity of the liquid obtained via the first and second electrodes 106, 108, and temperature of the liquid obtained by the thermal sensor 110.

In some embodiments, the computing device 130 may include a processing unit 140 coupled to the circuitry 116 to process the electrical parameters to determine the quality of the liquid based on the electrical and thermal parameters of the liquid. The processing unit 140 may include a processor 132 configured to process the electrical and thermal parameters. The processing unit 140 may include memory 134 having instructions (e.g., compiled in a control module 150) that, when executed on the processor 132, may cause the processing unit 140 to perform liquid parameters processing, for example, calculating liquid quality as described above. The computing device 130 may include other components necessary for the functioning of the computing device 130. For example, the computing device 130 may include a display 144 configured to display at least the results of the liquid quality measurements provided by the processing unit 140, a radio 148 to transmit liquid quality measurements or the electrical and/or thermal parameters for further processing, and a battery 146 configured to provide power supply to the computing device 130 and/or the apparatus 100.

As discussed, the control module 150 may be implemented as a software component stored, e.g., in the memory 134 and configured to execute on the processor 132. In some embodiments, the control module 150 may be implemented as a combination of software and hardware components. In some embodiments, the control module 150 may include a hardware implementation.

The processor 132, memory 134, and other components of the computing device 130 may be coupled with one or more interfaces (not shown) configured to facilitate information exchange among the above-mentioned components. Communications interface(s) (not shown) may provide an interface for the device 100 to communicate over one or more wired or wireless network(s) and/or with any other suitable device. In some embodiments, the PCB 102 may include some or all hardware components that are necessary for functioning of the computing device 130, in addition to 106, 108, and 110 described above. In some embodiments, the PCB 102 may include the above elements and communicatively couple with the device 130 via wireless or wired connection 128. An example configuration of the apparatus 100 including a computing device 130 will be described below in greater detail.

Figure 2:
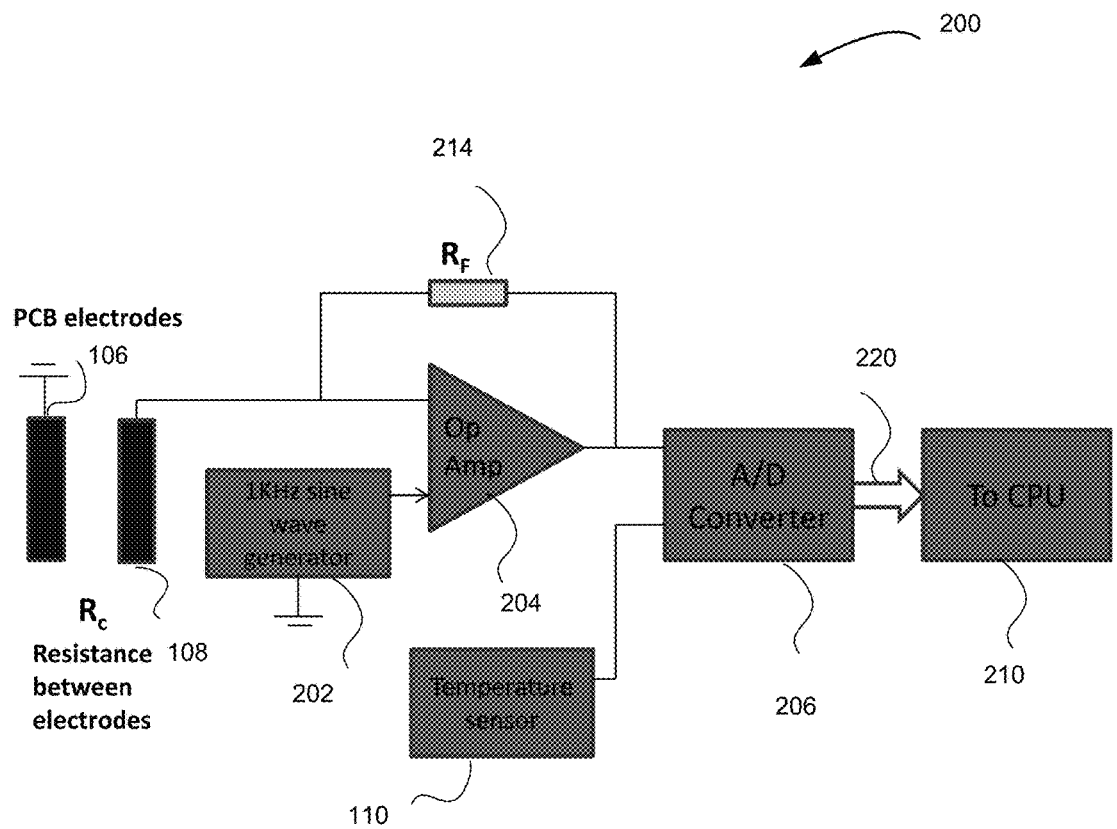
FIG. 2 is a schematic representation of an example implementation of the circuitry to process liquid parameters, in accordance with some embodiments.

FIG. 2 is a schematic representation 200 of an example implementation of the circuitry 116, in accordance with some embodiments. The schematic representation 200 may include a sine wave generator 202 to generate a sine wave signal, for example, about 1 KHz sine wave. The sine wave may be generated, for example, by a local oscillator or by a digital to analog converter, or by toggling a digital port pin of a microcontroller.

The schematic representation 200 may further include an amplifier 204 coupled with the sine wave generator 202 and the first and second electrodes 106, 108, as shown, to amplify and modulate the generated sine wave signal based at least in part on an input signal from the first and second electrodes 106, 108. The amplifier 204 may have a feedback resistor Rf 214 placed in series with the amplifier 204. The input signal may be fed to the input of the amplifier 204. The input signal may correspond to resistance between the first and second electrodes 106, 108.

For example, when the electrodes 106, 108 are immersed in water, the emerged resistance between the electrodes Rc (and consequently, electrical conductivity of the liquid) may correspondingly alter the amplification of the sine wave at the output of the amplifier 204. The other input signal may be input to the analog-to-digital converter 206 from the thermal sensor 110, as shown, to account for thermal influence on the liquid's electrical conductivity as described above. More specifically, the peak to peak amplitude of the sine wave at the output of the amplifier 204 may be directly proportional to the electrical conductivity of the liquid (e.g., water) and correspondingly to its TDS value. The schematic representation 200 may further include an analog-to-digital converter 206 to receive and convert the modulated sine wave signal into a digital form. The converted signal 220 may be provided to an output unit 210 (e.g., a transmitter) that may provide the signal 220 to a processing unit, e.g., similar to processing unit 140, for further processing.

Figures 3, 4:
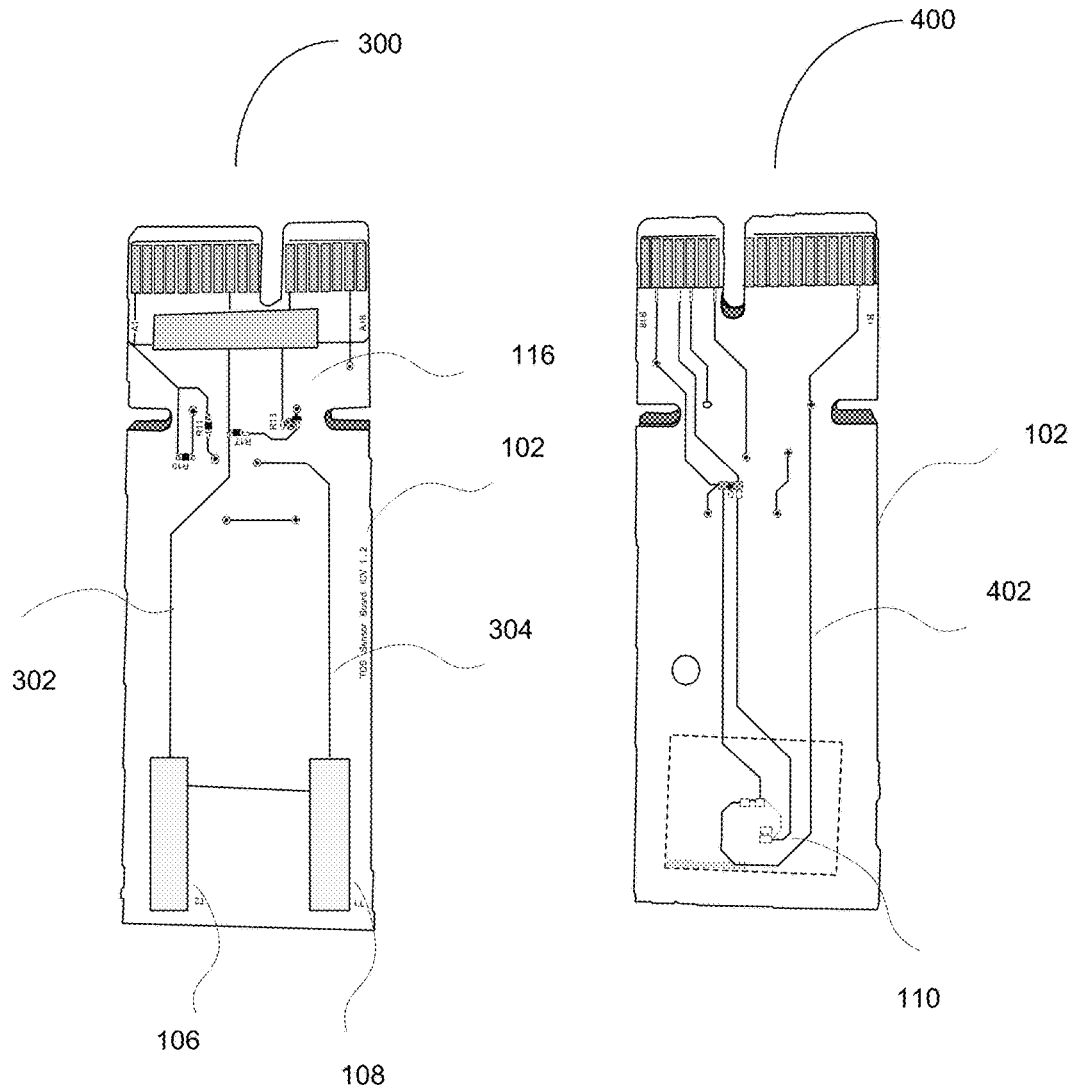
FIGS. 3 and 4 are example diagrams illustrating a front view and a back view of an example printed circuit board (PCB) configured as described in reference to FIG. 1, in accordance with some embodiments.

FIGS. 3 and 4 are example diagrams illustrating a front view 300 and a back view 400 of an example PCB configured as described in reference to FIG. 1, in accordance with some embodiments. More specifically, a PCB (e.g., PCB 102) may include electrodes 106, 108 patterned on the PCB 102 substrate, e.g., on the front side of the PCB 102, as shown. The thermal sensor 110 may also be mounted on the PCB 102 (e.g., on the back surface of the PCB 102). The electrodes 106 and 108 and thermal sensor 110 may be connected with the circuitry 116 via connecting lines 302, 304, 402 (implementing communicative connections 120), respectively. It should be noted that placing the electrodes 106, 108 on one side of the PCB 102 and the thermal sensor 110 on the other side of the PCB 102 is shown for illustrative purposes only. Other arrangements are also possible, e.g., placing the electrodes 106, 108 and the thermal sensor 110 on the same side of the PCB 102. As described above, the PCB 102 may include embedded electronic components of the device 100 described in reference to FIG. 1, such as, for example, a smartphone.

Figure 5:
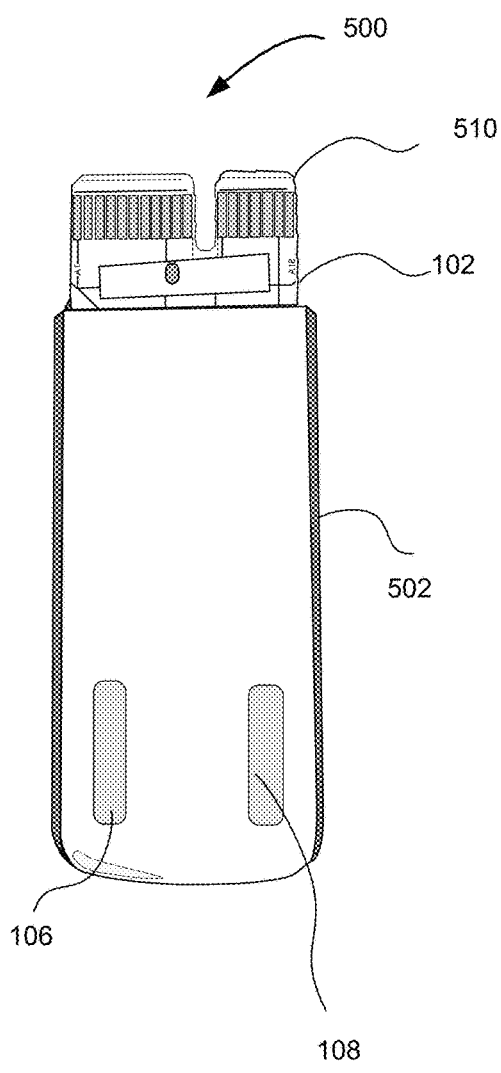
FIGS. 5 and 6 are example diagrams illustrating a front view and a back view of an example PCB configured as described in reference to FIG. 1 with a cover, in accordance with some embodiments.
Figure 6:
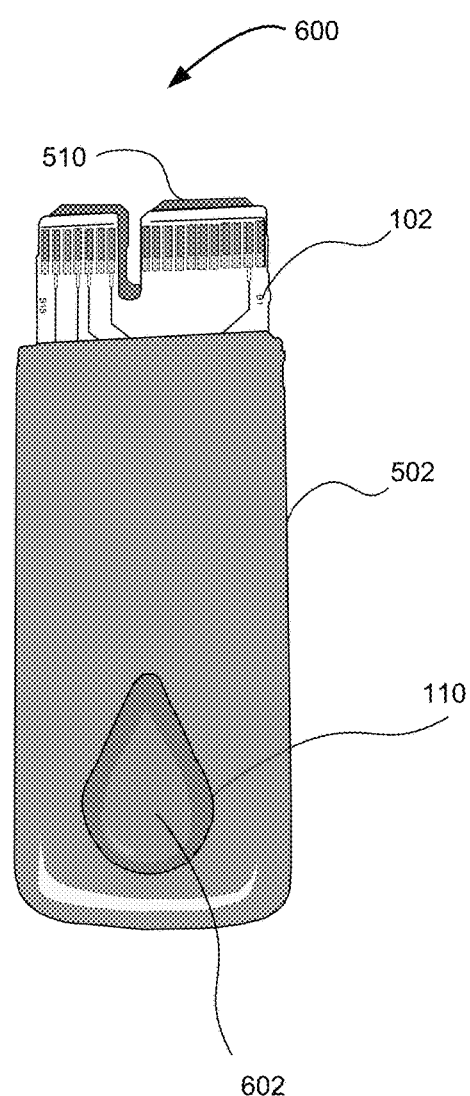

FIGS. 5 and 6 are example diagrams illustrating a front view 500 and a back view 600 of an example PCB configured as described in reference to FIG. 1 and shown with a cover, in accordance with some embodiments. As shown, the cover 502 may substantially cover the PCB 102, in some embodiments, leaving PCB edge connectors 510 exposed for connecting with a computing device, such as device 130, or connecting with one or more components of the device 100 as described in reference to FIG. 1.

In some embodiments, the thermal sensor 110 (not visible in FIG. 6 because of the cover 502) may be covered, e.g., with a cover portion 602, to protect the thermal sensor 110 from the liquid and to provide thermal exposure to the liquid on behalf of the thermal sensor, when at least a portion of the device 100 including the PCB 102 is exposed to the liquid. More specifically, the thermal sensor 110 may be encapsulated and/or sealed, e.g., using a thin metal/plastic can comprising the cover portion 602, to prevent direct contact with the liquid substance and at the same time thermally expose the sensor for temperature measurements. As shown, the electrodes 106, 108 may be exposed by the cover 502 to directly contact with a liquid to obtain a plurality of electrical parameters of the liquid when electrical current passes between the electrodes 106, 108 while in contact with the liquid.

Figure 7:
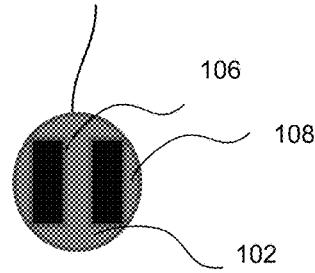
FIGS. 7-9 illustrate an example of a liquid quality meter configured to provide liquid quality measurements in accordance with some embodiments.
Figure 9:
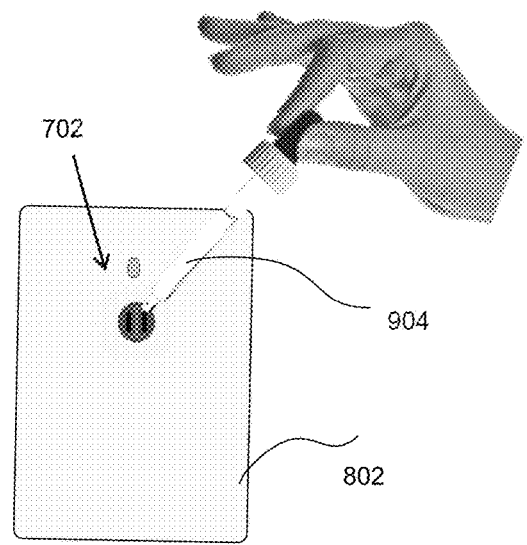
Figure 8:
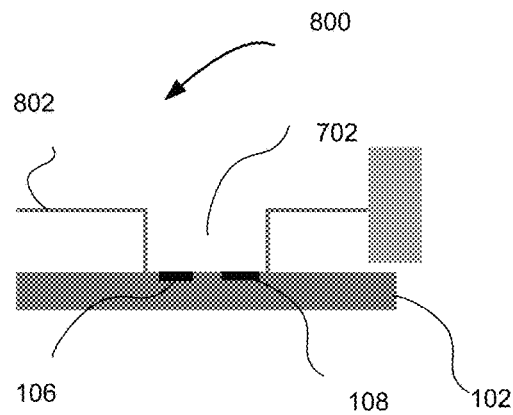

Besides the embodiments described above, there may be numerous variants of placing the electrodes on a PCB to provide direct contact with the liquid and placing the thermal sensor to provide thermal exposure to the liquid, for the PCB integrated with a computing device. FIGS. 7-9 illustrate an example of a liquid quality meter configured to provide liquid quality measurements in accordance with embodiments described above. More specifically, FIGS. 7-9 illustrate a liquid quality meter wherein the electrodes are disposed on a PCB to provide direct contact with the liquid, and the thermal sensor is placed on the PCB to provide thermal contact with liquid, wherein the PCB is integrated with a computing device.

FIGS. 7 and 8 illustrate a top view 700 and a cross-section 800 of a PCB (e.g., PCB 102) integrated with a computing device (not shown) having the electrodes 106, 108 patterned on the PCB 102 as described above and exposed by a cover 802 of the computing device to provide direct contact with a liquid when desired. As shown, the cover 802 may include an opening 702, such as a substantially circular depression ("well") on a back side of the cover 802 to allow the electrodes 106, 108 to directly contact the liquid. The electrodes 106, 108 may be embedded inside the depression ("well").

The method of use of liquid quality measurements by a liquid quality meter implemented as described in reference to FIGS. 7 and 8 is illustrated in FIG. 9. As shown, liquid 904 may be provided (e.g., administered with a drip or pipette as shown, or dripped into the opening 702 by other methods, e.g., using one's fingers) to the surfaces of the electrodes 106, 108 through the opening 702 of the cover 802 of an apparatus hosting the PCB 102, such as a smartphone (not shown), comprising the liquid quality meter. It should be noted that the thermal sensor 110 (not shown) may be disposed around the opening 702 on the PCB 102, to provide the thermal contact with the liquid 904. After completing liquid quality measurements, the user may wipe the liquid from the "well."

Figure 10:
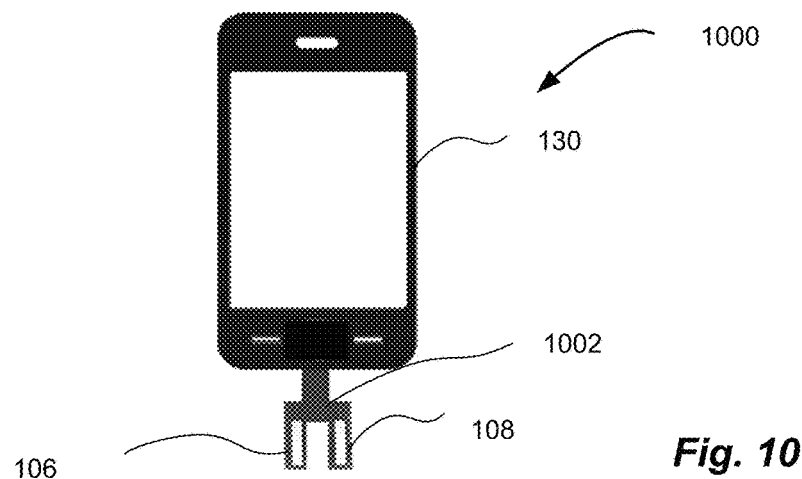
FIGS. 10-11 illustrate other examples of a liquid quality meter configured to provide liquid quality measurements in accordance with some embodiments.
Figure 11:
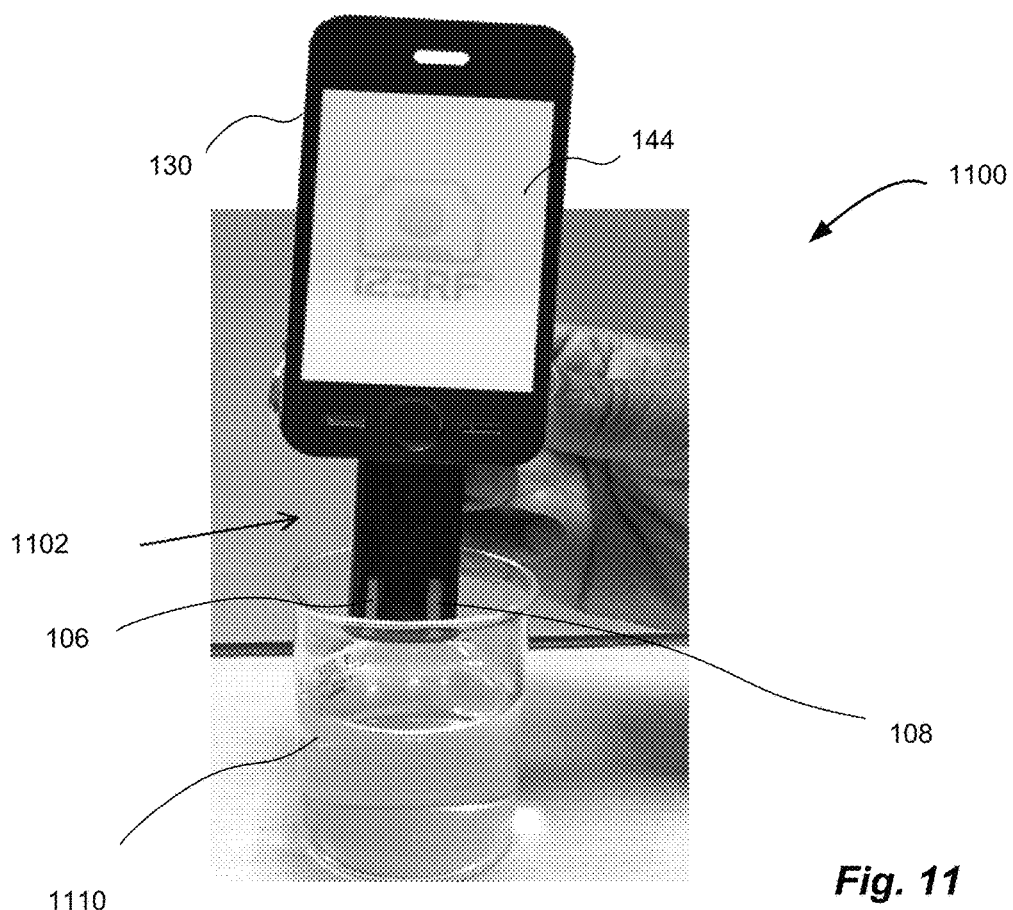

FIGS. 10-11 illustrate examples 1000 and 1100 of a liquid quality meter configured to provide liquid quality measurements in accordance with embodiments described above. As shown in FIG. 10, the electrodes 106, 108 may be disposed on a PCB substrate 1002, which may be extendable from the apparatus hosting the liquid quality meter, such as computing device 130 (e.g., a smartphone). The electrodes 106, 108 may be communicatively coupled with the circuitry 116 that may be disposed on the PCB 102 (not shown) placed inside the computing device 130.

As illustrated in FIG. 11, the electrodes 106, 108 may be disposed on a PCB 1102, similar to the embodiments described in reference to FIGS. 3-4. The PCB 1102 may either be extendable from or pluggable into the apparatus hosting the PCB 1102, such as computing device 130 (e.g., a smartphone). As shown, at least a portion of the PCB 1102 with electrodes 106, 108 may be extended from the device 100, to be inserted into liquid 1110. The resulting liquid quality measurements may be displayed to a user on the display 144 of the computing device 130.

Figure 12:
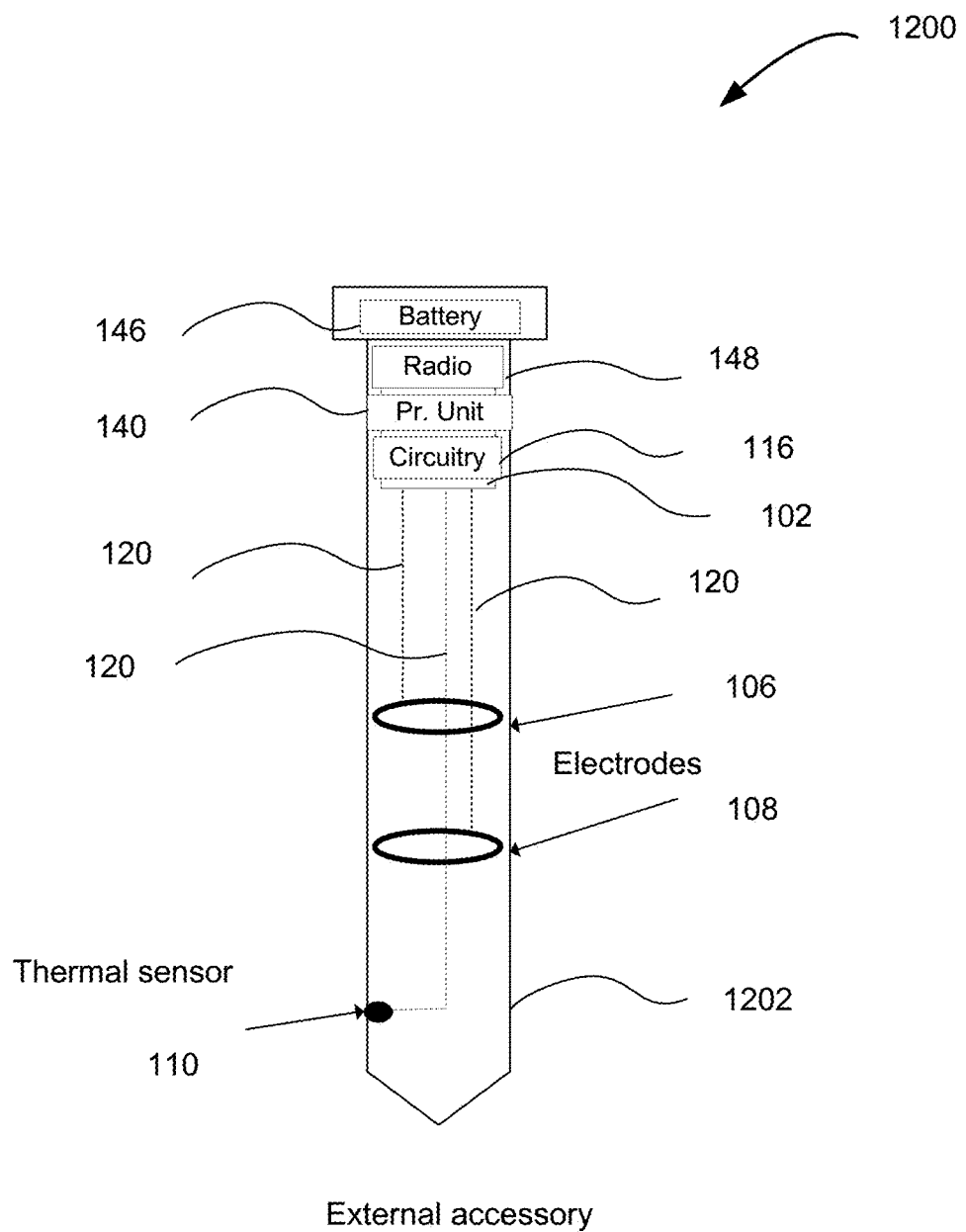
FIG. 12 illustrates another example of a liquid quality meter configured to provide liquid quality measurements in accordance with some embodiments.

FIG. 12 illustrates another example of a liquid quality meter 1200 configured to provide liquid quality measurements in accordance with embodiments described above. For example, the liquid quality meter 1200 may be integrated with an external accessory to a computing device, for example, with a stylus 1202 associated with a tablet computer or a smartphone.

In this example, the electrodes 106, 108 may be disposed about a body of the stylus 1202. As shown, the electrodes 106, 108 may comprise metallic rings placed on the outer surface of the stylus 1202 and associated (e.g., communicatively coupled 120) with the PCB 102. For example, the electrodes 106, 108 may be created on a flexible polymer PCB wrapped around the inner surface or outer surface of stylus 1202. In another example, the electrodes 106, 108 may be screen printed on the surface of the stylus 1202. The thermal sensor 110 may be disposed inside the body of the stylus 1202, e.g., near the inside surface of the body, to provide thermal contact with the liquid, and communicatively coupled 120 with the PCB 102.

The PCB 102 may include other components associated with the stylus's functionality and providing for functionality of the liquid quality meter 1200. For example, as described in reference to FIG. 1, the components may include circuitry 116, processing unit 140, radio 148, and battery 146.

In operation, at least a portion of the stylus including the electrodes 106, 108 may be inserted into the liquid, in order to obtain electrical and thermal parameters of the liquid. The parameters may be collected by the circuitry 116, processed by the processing unit 140, and transmitted to the computing device for derivation of the liquid quality value by the radio 148.

Figure 13:
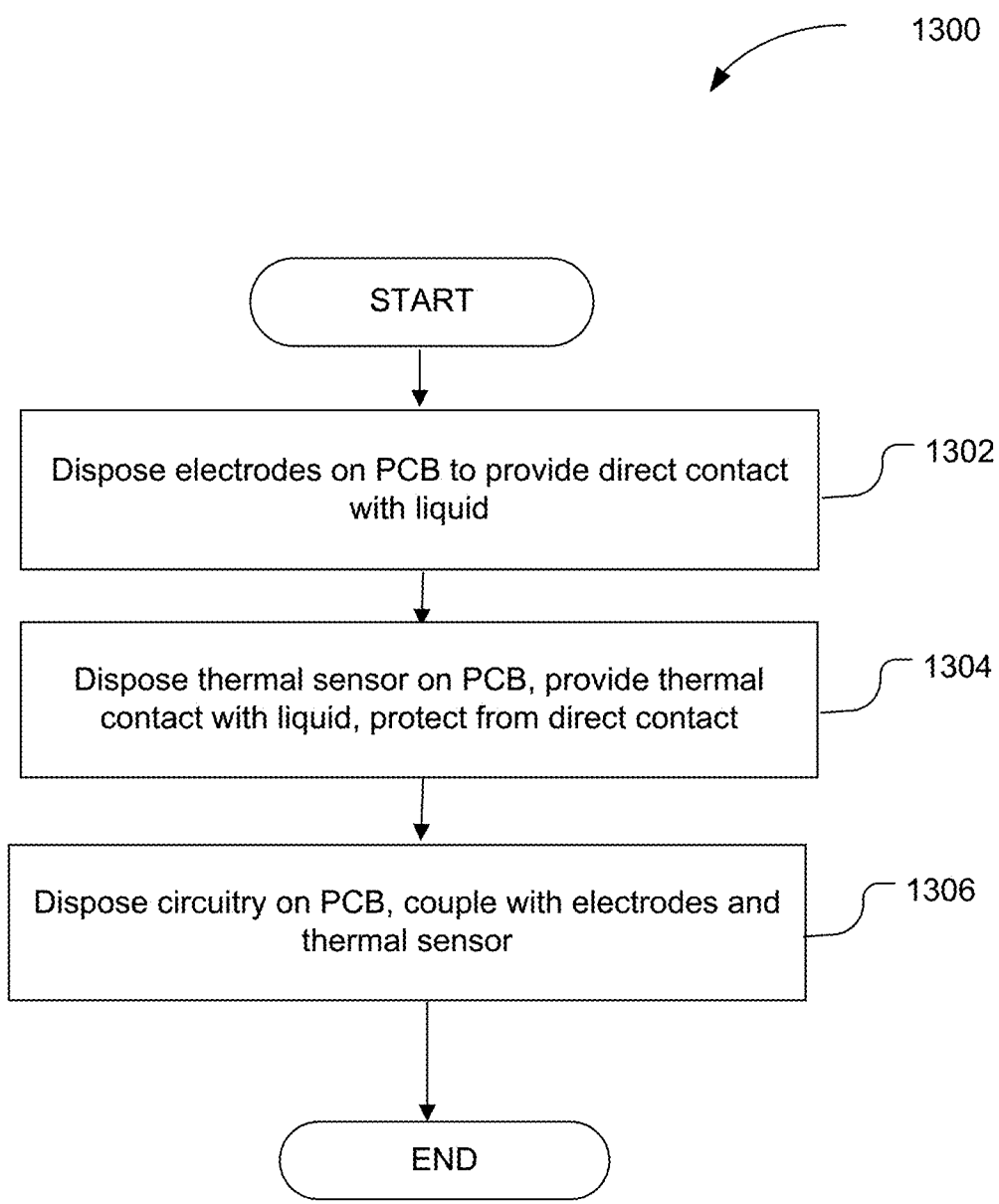
FIG. 13 is a process flow diagram for forming a PCB that may be integrated with a computing device to provide for liquid quality measurements as described in reference to FIG. 1, in accordance with some embodiments.

FIG. 13 is a process flow diagram 1300 for forming a PCB that may be integrated with a computing device to provide for liquid quality measurements as described in reference to FIG. 1, in accordance with some embodiments.

The process 1300 may begin at block 1302, where electrodes (e.g., 106, 108) may be disposed on a PCB (e.g., PCB 102) to directly contact a liquid to obtain electrical parameters of the liquid when electrical current passes between the electrodes 106, 108 while in contact with the liquid. In some embodiments, the electrodes 106, 108 may be prepared to be disposed on the PCB. For example, before the disposing the electrodes on the PCB, a layer of anti-corrosion metal (e.g., gold) may be deposited on a surface of the electrodes 106, 108.

At block 1304, a thermal sensor (e.g., 110) may be disposed on the PCB to be thermally coupled with liquid to measure thermal parameters of the liquid. At the same time, the thermal sensor may be protected from direct contact with the liquid. For example, the thermal sensor 110 may be encapsulated with a protective cover and/or sealed, to protect the thermal sensor and provide thermal coupling with the liquid. As described before, the electrical and thermal parameters may be associated with and used for computing the quality of the liquid.

At block 1306, circuitry (e.g., 116) may be disposed on the PCB. The disposing may include coupling the circuitry 116 with the electrodes 106, 108 to collect the electric parameters of the liquid.

Figure 14:
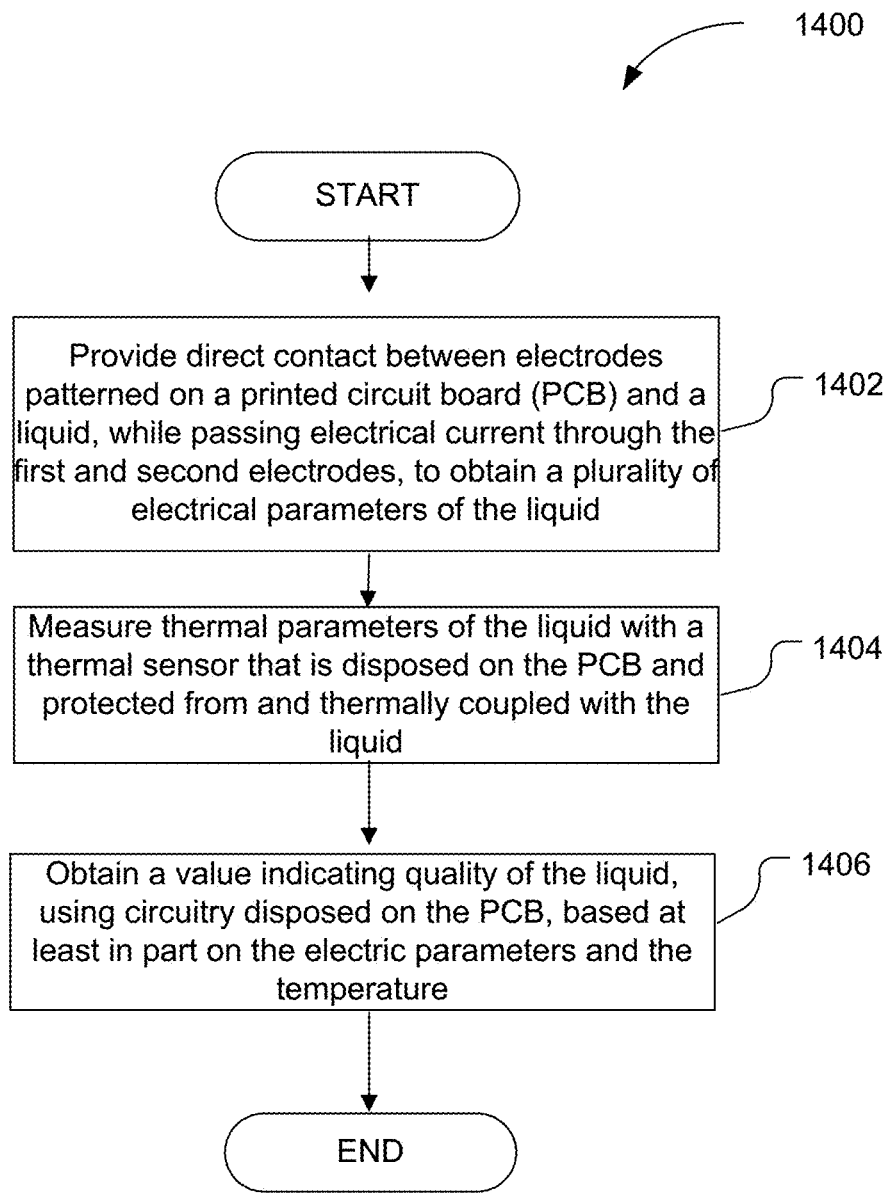
FIG. 14 is a process flow diagram for use of a liquid quality meter, in accordance with some embodiments.

FIG. 14 is a process flow diagram 1400 for use of a liquid quality meter, in accordance with some embodiments.

The process 1400 may begin at block 1402, where direct contact between the electrodes (e.g., 106, 108) patterned on a PCB (e.g., 102) and a liquid may be provided, while electrical current may be passing through the electrodes, to obtain electrical parameters of the liquid. The provision of direct contact between the electrodes 106, 108 and the liquid may be provided via any one of the ways described in reference to FIGS. 9, 11, and 12.

At block 1404, thermal parameters of the liquid may be measured with a thermal sensor (e.g., 110) disposed on the PCB. As described above, the thermal sensor 110 may be protected from and thermally coupled with the liquid.

At block 1406, a value indicating quality of the liquid may be obtained, using circuitry disposed on the PCB, based at least in part on the electric and thermal parameters of the liquid.

Figure 15:
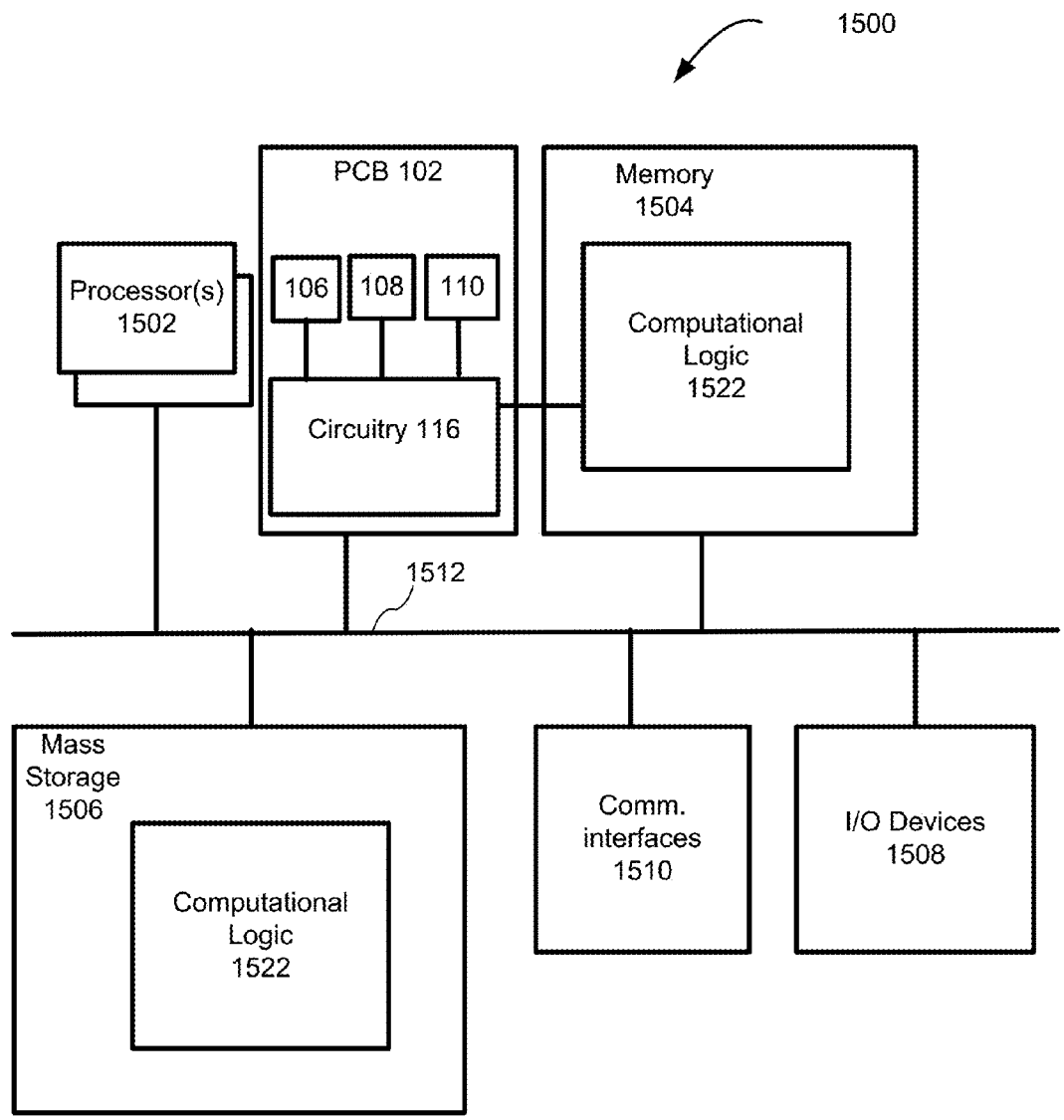
FIG. 15 illustrates an example computing device suitable for use with various components of FIG. 1, such as computing device of FIG. 1, in accordance with various embodiments.

FIG. 15 illustrates an example computing device 1500 suitable for use with various components of FIG. 1, such as apparatus 100 including computing device 130 of FIG. 1, in accordance with various embodiments. As shown, computing device 1500 may include one or more processors or processor cores 1502 and system memory 1504. For the purpose of this application, including the claims, the terms "processor" and "processor cores" may be considered synonymous, unless the context clearly requires otherwise. The processor 1502 may include any type of processors, such as a central processing unit (CPU), a microprocessor, and the like. The processor 1502 may be implemented as an integrated circuit having multi-cores, e.g., a multi-core microprocessor. The computing device 1500 may include mass storage devices 1506 (such as diskette, hard drive, volatile memory (e.g., dynamic random-access memory (DRAM), compact disc read only memory (CD-ROM), digital versatile disk (DVD), and so forth). In general, system memory 1504 and/or mass storage devices 1506 may be temporal and/or persistent storage of any type, including, but not limited to, volatile and non-volatile memory, optical, magnetic, and/or solid state mass storage, and so forth. Volatile memory may include, but is not limited to, static and/or dynamic random access memory. Non-volatile memory may include, but is not limited to, electrically erasable programmable read-only memory, phase change memory, resistive memory, and so forth.

The computing device 1500 may further include input/output devices 1508 (such as a display (e.g., a touchscreen display similar to 144), keyboard, cursor control, remote control, gaming controller, image capture device, and so forth) and communication interfaces 1510 (such as network interface cards, modems, infrared receivers, radio receivers (e.g., Bluetooth), and so forth).

The communication interfaces 1510 may include communication chips (not shown) that may be configured to operate the device 1500 in accordance with a Global System for Mobile Communication (GSM), General Packet Radio Service (GPRS), Universal Mobile Telecommunications System (UMTS), High Speed Packet Access (HSPA), Evolved HSPA (E-HSPA), or Long-Term Evolution (LTE) network. The communication chips may also be configured to operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). The communication chips may be configured to operate in accordance with Code Division Multiple Access (CDMA), Time Division Multiple Access (TDMA), Digital Enhanced Cordless Telecommunications (DECT), Evolution-Data Optimized (EV-DO), derivatives thereof, as well as any other wireless protocols that are designated as 3G, 4G, 5G, and beyond. The communication interfaces 1510 may operate in accordance with other wireless protocols in other embodiments.

The above-described computing device 1500 elements may be coupled to each other via system bus 1512, which may represent one or more buses. In the case of multiple buses, they may be bridged by one or more bus bridges (not shown). Each of these elements may perform its conventional functions known in the art. In particular, system memory 1504 and mass storage devices 1506 may be employed to store a working copy and a permanent copy of the programming instructions implementing the operations' associated liquid quality measurements, such as instructions described in reference to the control module 150 of FIG. 1. The various elements may be implemented by assembler instructions supported by processor(s) 1502 or high-level languages that may be compiled into such instructions.

The permanent copy of the programming instructions may be placed into permanent storage devices 1506 in the factory, or in the field, through, for example, a distribution medium (not shown), such as a compact disc (CD), or through communication interface 1510 (from a distribution server (not shown)). That is, one or more distribution media having an implementation of the agent program may be employed to distribute the agent and to program various computing devices.

The number, capability, and/or capacity of the elements 1508, 1510, 1512 may vary, depending on whether computing device 1500 is used as a stationary computing device, such as a set-top box or desktop computer, or a mobile computing device, such as a tablet computing device, laptop computer, game console, or smartphone. Their constitutions are otherwise known, and accordingly will not be further described.

At least one of processors 1502 may be packaged together with computational logic 1522 configured to practice aspects of embodiments described in reference to FIGS. 1-14. For one embodiment, at least one of processors 1502 may be packaged together with computational logic 1522 configured to practice aspects of liquid quality measurements to form a System in Package (SiP) or a System on Chip (SoC). For at least one embodiment, the SoC may be utilized in, e.g., but not limited to, a mobile computing device such as a computing tablet or smartphone. For example, computational logic 1522 may be associated with, or otherwise configured to include or access, a control module similar to the control module 150 described in reference to FIG. 1.

The computing device 1500 may include or otherwise associate with a PCB, such as PCB 102 having electrodes 106, 108, thermal sensor 110, and circuitry 116 for collecting electrical and thermal parameters of the liquid as described above. In some embodiments, the PCB 102 may include some or all of the elements 1502, 1504, 1506, 1508, and 1510, necessary for functioning of the computing device 1500. In some embodiments, the PCB 102 may be communicatively coupled with the computing device 1500 as described in reference to FIG. 1.

In various implementations, the computing device 1500 may comprise a laptop, a netbook, a notebook, an ultrabook, a smartphone, a tablet, a personal digital assistant (PDA), an ultra mobile PC, a mobile phone, or a digital camera. In further implementations, the computing device 1500 may be any other electronic device that processes data.

The embodiments described herein may be further illustrated by the following examples. Example 1 is printed circuit board (PCB) for measuring quality of liquid, comprising: first and second electrodes disposed on the PCB to directly contact with a liquid to obtain a plurality of electrical parameters of the liquid when electrical current passes between the first and second electrodes while in contact with the liquid, wherein the electrical parameters are associated with quality of the liquid; and circuitry disposed on the PCB and coupled to the first and second electrodes to collect the electrical parameters of the liquid.

Example 2 may include the subject matter of Example 1, and further specifies that the apparatus further includes a thermal sensor disposed on the PCB to thermally contact the liquid to obtain one or more thermal parameters of the liquid, wherein the one or more thermal parameters are also associated with the quality of the liquid, wherein the circuitry is further coupled with the thermal sensor to collect the thermal parameters.

Example 3 may include the subject matter of Example 2, and further specifies that the first and second electrodes are embedded on one side of the PCB, and the thermal sensor is mounted on another side of the PCB.

Example 4 may include the subject matter of Example 3, and further specifies that the thermal sensor is encapsulated with a cover to protect the thermal sensor from the liquid and to provide thermal exposure to the liquid on behalf of the thermal sensor.

Example 5 may include the subject matter of Example 2, and further specifies that the thermal parameters comprise temperature.

Example 6 may include the subject matter of Example 2, and further specifies that the apparatus may further include a processing unit coupled to the circuitry to process the electrical parameters to determine the quality of the liquid based at least in part on the electric and thermal parameters of the liquid.

Example 7 may include the subject matter of Example 1, and further specifies that the electric parameters include electric conductivity of the liquid, and wherein the quality of the liquid comprises a value indicating total dissolved salts (TDS) in the liquid.

Example 8 may include the subject matter of Example 7, and further specifies that liquid comprises water.

Example 9 may include the subject matter of Example 1, and further specifies that the first and second electrodes are embedded in a PCB substrate and wherein the first and second electrodes are chemical or electrochemical plated.

Example 10 may include the subject matter of any of Example 1 to 9, and further specifies that the circuitry includes: a sine wave generator to generate a sine wave signal; an amplifier coupled with the sine wave generator and the first and second electrodes to amplify and modulate the generated sine wave signal based at least in part on an input signal from the first and second electrodes, wherein the input signal corresponds to resistance between the first and second electrodes; and an analog-to-digital converter to receive and convert the modulated sine wave signal into a digital form.

Example 11 may include an apparatus for measuring quality of liquid, comprising: a printed circuit board (PCB) having first and second electrodes associated with the PCB, to directly contact with a liquid to obtain a plurality of electrical parameters of the liquid when electrical current passes between the first and second electrodes while in contact with the liquid, wherein the electrical parameters are associated with quality of the liquid; and wherein the PCB further comprises circuitry disposed thereon and coupled to the first and second electrodes to collect the electric parameters of the liquid.

Example 12 may include the subject matter of Example 11, and further specifies that the apparatus comprises a liquid quality meter integrated with a portable special purpose device.

Example 13 may include the subject matter of Example 11, and further specifies that the apparatus may further comprise computing or communication components, and wherein the apparatus comprises one of a smartphone, a tablet computer, or a laptop computer.

Example 14 may include the subject matter of Example 11, and further specifies that the apparatus may further comprise a cover to enclose the PCB, wherein the cover includes an opening to allow the first and second electrodes to directly contact the liquid.

Example 15 may include the subject matter of Example 11, and further specifies that the apparatus further comprises a thermal sensor disposed on the PCB and thermally coupled to the liquid substance to measure one or more thermal parameters of the liquid substance, wherein the one or more thermal parameters are associated with the quality of the liquid.

Example 16 may include the subject matter of Example 15, and further specifies that the apparatus may further comprise a cover to enclose the PCB, wherein the cover comprises a circular depression on a back side of the cover, wherein the thermal sensor is disposed around the circular depression.

Example 17 may include the subject matter of Example 11, and further specifies that the PCB is extendable from the apparatus or pluggable into the apparatus.

Example 18 may include the subject matter of any of Examples 11 to 17, and further specifies that the electrodes are patterned on the PCB.

Example 19 may include the subject matter of Example 11, and further specifies that the apparatus may comprise an external accessory to a computing device, wherein the accessory comprises a stylus, wherein the first and second electrodes are disposed about a body of the stylus and communicatively coupled with the PCB.

Example 20 may include a method for making a quality of liquid measuring apparatus, comprising: disposing first and second electrodes on a printed circuit board (PCB) to directly contact a liquid to obtain a plurality of electrical parameters of the liquid when electrical current passes between the first and second electrodes while in contact with the liquid, wherein the plurality of electrical parameters are associated with quality of the liquid; and disposing circuitry on the PCB, the disposing including coupling the circuitry with the first and second electrodes to collect the electric parameters of the liquid.

Example 21 may include the subject matter of Example 20, and further specifies that the method may include disposing a thermal sensor on the PCB to be thermally coupled with the liquid to measure one or more thermal parameters of the liquid, wherein the one or more thermal parameters are associated with the quality of the liquid.

Example 22 may include the subject matter of Example 21, and further specifies that the method may include depositing a layer of anti-corrosion metal on a surface of the first and second electrodes, before the disposing the electrodes on the PCB; and encapsulating the thermal sensor with a protective cover, to protect the thermal sensor and provide thermal coupling with the liquid.

Example 23 may include a method for operating a quality of liquid measuring apparatus, comprising: directly contacting first and second electrodes patterned on a printed circuit board (PCB) with a liquid, while passing electrical current through the first and second electrodes, to obtain a plurality of electrical parameters of the liquid; substantially concurrently measuring thermal parameters of the liquid with a thermal sensor that is disposed on the PCB and protected from and thermally coupled with the liquid; and obtaining a value indicating quality of the liquid, using circuitry disposed on the PCB, based at least in part on the electric parameters and the thermal parameters.

Example 24 may include the subject matter of Example 23, and further specifies that directly contacting includes one of: extending the PCB from an apparatus hosting the PCB, and inserting at least a portion of the PCB having the first and second electrodes into the liquid; plugging the PCB in an apparatus to host the PCB; or providing the liquid on first and second surfaces of the first and second electrodes through an opening of a cover of the apparatus hosting the PCB.

Example 25 may include the subject matter of Example 24, and further specifies that the apparatus comprises a smartphone, a tablet computer, or a laptop computer having the PCB with the first and second electrodes, the thermal sensor, and the circuitry for obtaining the value indicating the quality of the liquid, wherein directly contacting, substantially concurrently measuring, and obtaining are performed using the smartphone, the tablet computer, or the laptop computer.

Various operations are described as multiple discrete operations in turn, in a manner that is most helpful in understanding the claimed subject matter. However, the order of description should not be construed as to imply that these operations are necessarily order dependent. Embodiments of the present disclosure may be implemented into a system using any suitable hardware and/or software to configure as desired.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims and the equivalents thereof.

What is claimed is:

1. A printed circuit board (PCB), comprising:
   first and second electrodes disposed on the PCB to directly contact with a liquid to obtain one or more electrical parameters of the liquid when electrical current passes between the first and second electrodes while in contact with the liquid, wherein the electrical parameters are associated with quality of the liquid; and
   circuitry disposed on the PCB and coupled to the first and second electrodes to collect at least the electrical parameters of the liquid, wherein the circuitry includes: a sine wave generator to generate a sine wave signal; an amplifier coupled with the sine wave generator and at least one of the first and second electrodes to amplify and modulate the generated sine wave signal based at least in part on an input signal from the first and second electrodes, wherein the input signal corresponds to a resistance between the first and second electrodes; and an analog-to-digital converter to receive and process at least the modulated sine wave signal.

2. The PCB of claim 1, wherein the first and second electrodes are embedded in a substrate of the PCB and wherein the first and second electrodes are chemical or electrochemical plated.

3. The PCB of claim 1, wherein the electrical parameters include electric conductivity of the liquid, and wherein the quality of the liquid comprises a value indicating total dissolved salts (TDS) in the liquid.

4. The PCB of claim 3, wherein the liquid comprises water.

5. The PCB of claim 1, further comprising:
   a thermal sensor disposed on the PCB to thermally contact the liquid to obtain one or more thermal parameters of the liquid, wherein the one or more thermal parameters are also associated with the quality of the liquid and are different than the one or more electrical parameters, wherein the circuitry is further coupled with the thermal sensor to collect the thermal parameters.

6. The PCB of claim 5, wherein the thermal parameters comprise temperature.

7. The PCB of claim 5, further comprising:
a processing unit coupled to the circuitry to process the electrical parameters to determine the quality of the liquid based at least in part on the electrical and thermal parameters of the liquid.

8. The PCB of claim 5, wherein the first and second electrodes are embedded on one side of the PCB, and the thermal sensor is mounted on another side of the PCB.

9. The PCB of claim 8, wherein the thermal sensor is encapsulated with a cover to protect the thermal sensor from the liquid and to provide thermal exposure to the liquid on behalf of the thermal sensor.

10. A method, comprising:
disposing first and second electrodes on a printed circuit board (PCB) to directly contact a liquid to obtain one or more electrical parameters of the liquid when electrical current passes between the first and second electrodes while in contact with the liquid, wherein the plurality of electrical parameters are associated with quality of the liquid; and
disposing circuitry on the PCB, the disposing including:
coupling an amplifier of the circuitry with a sine wave generator and at least one of the first and second electrodes to amplify and modulate the generated sine wave signal based at least in part on an input signal from the first and second electrodes, and connecting an output of the amplifier with an analog-to-digital converter, wherein the analog-to-digital converter is to receive and process at least the modulated sine wave signal, wherein the input signal corresponds to a resistance between the first and second electrodes.

11. The method of claim 10, further comprising:
disposing a thermal sensor on the PCB to be thermally coupled with the liquid to measure one or more thermal parameters of the liquid, wherein the one or more thermal parameters are associated with the quality of the liquid and are different than the one or more electrical parameters.

12. The method of claim 11, further comprising:
depositing a layer of anti-corrosion metal on a surface of the first and second electrodes, before the disposing the electrodes on the PCB; and
encapsulating the thermal sensor with a protective cover, to protect the thermal sensor and provide thermal coupling with the liquid.

* * * * *